United States Patent [19]

Inoue et al.

[11] Patent Number: 5,241,106

[45] Date of Patent: Aug. 31, 1993

[54] PROCESS FOR PRODUCING ETHYL ACETATE

[75] Inventors: Kaoru Inoue; Masao Iwasaki; Kazuaki Matsui, all of Kanagawa, Japan

[73] Assignee: Mitsui Toatsu Chemicals, Inc., Tokyo, Japan

[21] Appl. No.: 963,390

[22] Filed: Oct. 19, 1992

[30] Foreign Application Priority Data

| Oct. 22, 1991 | [JP] | Japan | 3-273870 |
| Dec. 16, 1991 | [JP] | Japan | 3-331786 |
| Dec. 20, 1991 | [JP] | Japan | 3-338419 |
| Dec. 26, 1991 | [JP] | Japan | 3-344669 |
| Dec. 26, 1991 | [JP] | Japan | 3-344673 |

[51] Int. Cl.$^5$ ............... C07C 69/14; C07C 67/04
[52] U.S. Cl. ................................... 560/247; 502/213
[58] Field of Search ............... 560/247; 501/102, 103, 501/208, 210, 213

[56] References Cited

U.S. PATENT DOCUMENTS

| 3,362,987 | 1/1968 | Kronig | 560/247 |
| 3,678,099 | 7/1972 | Kemp | 560/247 |
| 4,275,228 | 6/1981 | Gruffaz et al. | 560/247 |
| 4,281,176 | 7/1981 | Gruffaz et al. | 560/247 |

FOREIGN PATENT DOCUMENTS

| 55-160745 | 12/1980 | Japan. |
| 56-30334 | 7/1981 | Japan. |
| 57-56045 | 4/1982 | Japan. |
| 58-43384 | 9/1983 | Japan. |
| 59-51337 | 12/1984 | Japan. |
| 60-17774 | 5/1985 | Japan. |
| 60-17775 | 5/1985 | Japan. |
| 61-249949 | 11/1986 | Japan. |
| 63-51060 | 10/1988 | Japan. |
| 2-52045 | 2/1990 | Japan. |
| 4-139148 | 5/1992 | Japan. |
| 4-139149 | 5/1992 | Japan. |

OTHER PUBLICATIONS

Kogyo Kagaku Zasshi (Journal of Japanese Industrial Chemistry), vol. 72, 1945–1948 (1969).
Kogyo Kagaku Zasshi (Journal of Japanese Industrial Chemistry), vol. 72, 1949–1953 (1960).

*Primary Examiner*—Arthur C. Prescott
*Attorney, Agent, or Firm*—Burns, Doane, Swecker & Mathis

[57] ABSTRACT

Ethyl acetate is produced in good yield by reacting ethylene with acetic acid in the presence of a catalyst comprising a tungstophosphoric acid of which 10–90% of the total amount of proton is replaced with a member selected from the group consisting of (a) cesium metal cation, (b) a combination of cesium metal cation and at least one cation selected from alkali metal cations other than cesium cation, and (c) a combination of cesium metal cation and at least one cation of iron group metal cations.

15 Claims, No Drawings

PROCESS FOR PRODUCING ETHYL ACETATE

BACKGROUND OF THE INVENTION

1. Field of the Invention

The present invention relates to a process for producing ethyl acetate, and more particularly, to a process for producing ethyl acetate by reacting ethylene with acetic acid in the presence of a catalyst.

Ethyl acetate may be used in a large amount for ethyl acetate coating materials, solvents, and starting material for producing various chemicals and industrial chemicals.

2. Description of the Related Art

As widely used industrial processes for producing ethyl acetate, heretofore there have been known a process comprising esterification of acetic acid with ethanol and a process comprising dimerization reaction of acetaldehyde in the presence of a metal alkoxide catalyst.

According to the production process using esterification, ethanol is used as a starting material in addition to acetic acid, and ethanol is commercially produced from ethylene for industrial use and therefore, is a secondary starting material. Moreover, ethanol is an expensive substance in Japan, Germany and others from the standpoint of national policy.

In addition, an esterification reaction is an equilibrium reaction so that it is necessary to remove co-produced water continuously from the reaction system by a certain method in order to achieve the high reaction conversion. These are problems concerning both starting materials and reaction efficiency. Therefore, there is much room for improvement.

According to the process involving dimerization of acetaldehyde (Tischtschenko reaction), the starting material, acetaldehyde, is a secondary starting material produced from ethylene. It is known that this dimerization reaction can proceed mildly and attain high conversion and selectivity.

However, a catalyst used in this reaction is usually a metal alkoxide such as aluminum alkoxide and the like, and the formation of acetaldol as a side reaction of the dimerization reaction and the subsequent dehydration reaction are inevitable. Water produced by the dehydration reaction easily decomposes the metal alkoxide catalyst. Therefore, this process suffers from problems as to the starting material and life of the catalsyt.

In view of the foregoing, as a new process for producing ethyl acetate, there have been recently researched vigorously a process for ethyl acetate starting from ethylene.

This process proceeds as a reaction of direct addition of ethylene to acetic acid and an acid catalyst is used.

For example, as a liquid phase catalytic reaction, Japanese Patent Application Laid-open No. 160745/1980 uses trifluoromethanesulfonic acid as a catalyst; Japanese Patent Publication No. 51060/1988 uses a metal cation-exchanged bentonite as a catalyst; and Japanese Patent Publication No. 30334/1981 uses a heteropoly acid of tungsten or its acidic metal salt soluble in the reaction media as a catalyst and a prescribed amount of water is added to the reaction system.

Among them, in the case of the process using a trifluoromethanesulfonic acid catalyst, the reaction results are good, but trifluoromethanesulfonic acid is expensive and very unstable and furthermore exhibits a very strong acidity. Therefore, this liquid phase homogeneous catalyst considerably corrodes reactors and the like.

Similarly, in the case of the process using a catalyst composed of a heteropoly acid of tungsten or its acidic metal salt which is a liquid phase uniform catalyst, corrosion occurs to a great extent and the catalytic activity is insufficient.

Further, though these liquid phase homogeneous catalysts can be easily separated from the product, ethyl acetate, it is very difficult to separate the liquid phase homogeneous catalysts from by-products formed during the reaction, in particular, high boiling point products. Therefore, recovery and regeneration of the catalysts are substantially not possible and as a result, the catalytic activity is disturbed and the life of catalyst is shortened.

In the case of the process using a catalyst composed of a metal cation-exchanged bentonite, a large amount of the catalyst should be used so as to achieve a high reaction yield and it is necessary to conduct the reaction at a temperature as high as 250° C. In other words, there is a drawback that the catalytic activity is extremely low.

In view of the foregoing situation, from the standpoint of process, a method for producing ethyl acetate in a gas phase fixed bed has been recently researched vigorously aiming at advantages such as easy separation of the product from catalyst, easy continuous operation, and simplification of the reaction apparatus. For example, the following catalysts have been proposed for the above-mentioned purpose.

Japanese Patent Publication No.17775/1985 discloses the production of ethyl acetate by using a catalyst carrying aromatic sulfonic acids on a carrier such as silica and the like.

Japanese Patent Publication No. 17774/1985 discloses a catalyst carrying sulfuric acid or diethylsulfuric acid on a silica carrier.

Japanese Patent Publication No. 43384/1983 discloses a catalyst composed on a solid fluorine containing polymer having sulfonic acid group as side chain functional groups (e.g. Nafion).

Further, Kougyo Kagaku Zasshi, Vol.72 No.9,1945(1969) discloses the production of ethyl acetate by reacting acetic acid with ethylene in a gas phase in the presence of a silica-supported tungstosilicic acid catalyst and a strongly acidic cation exchanging resin catalyst.

However, these catalysts for gas phase reactions have many problems so that any of these catalysts have not yet been used in an actual industrial production.

For example, a silica-supported sulfonic acids, sulfuric acid, or diethylsulfuric acid catalyst suffers from intense volatilization and dissolving-away of the catalytic effective components during the reaction, and therefore, it is not possible substantially to carry out a continuous operation for a long time.

Further, Nafion catalyst is very expensive and in addition, the catalyst is not stable at a temperature (200° C.) at which the reaction can be substantially carried out, and deterioration of the catalyst is inevitable.

Furthermore, catalytic activity of each of these catalysts is not sufficiently high and therefore, a very long reaction time is necessary when the reaction is effected at a low temperature and thereby the processes are not economical.

The tungstosilicic acid catalyst carried on silica and the strongly acidic cation exchange resin catalyst are not only of a low activity, but also the catalytic activity is lowered to a great extent within a very short time such as about two hours even at a temperature as low as about 150° C. and deactivation of the catalyst is observed.

In view of the foregoing, conventional catalysts for the production of ethyl acetate by the addition of acetic acid to ethylene have verious problems whether the catalysts are liquid phase reaction catalysts or gas phase reaction catalysts. As a result, the process for producing ethyl acetate directly from ethylene and acetic acid has not yet been commercially employed.

Therefore, from as industrial point of view, there is demanded a catalyst for producing ethyl acetate from ethylene and acetic acid which can be simply used from the standpoint of process technique and has high durability and high reaction activity.

SUMMARY OF THE INVENTION

One object of the present invention is to provide a process for producing efficiently ethyl acetate.

Another object of the present invention is to provide a process for producing ethyl acetate economically on an industrial scale.

A further object of the present invention to provide a process for producing ethyl acetate from ethylene and acetic acid in good conversion and selectivity.

Still another object of the present invention to provide a catalyst for producing ethyl acetate by reacting ethylene with acetic acid and capable of exhibiting at least partly good catalytic activity, durability and easy recovery.

According to one aspect of the present invention, there is provided a process for producing ethyl acetate comprising reacting ethylene with acetic acid in the presence of a catalyst comprising a tungstophosphoric acid of which 10–90% of the total amount of proton is replaced with a member selected from the group consiting of (a) cesium metal cation, (b) a combination of cesium metal cation and at least one cation selected from alkali metal cations other than cesium cation, and (c) a combination of cesium metal cation and at least one cation of iron group metal cations.

According to another aspect of the present invention, there is provided a catalyst for producing ethyl acetate by reacting ethylene with acetic acid which comprises a tungstophosphoric acid of which 10–90% of the total amount of proton is replaced with a member selected from the group consiting of (a) cesium metal cation, (b) a combination of cesium metal cation and at least one cation selected from alkali metal cations other than cesium cation, and (c) a combination of cesium metal cation and at least one cation of iron group metal cations.

DESCRIPTION OF THE PREFERRED EMBODIMENTS

According to the process of the present invention, ethyl acetate is produced by reacting ethylene with acetic acid in the presence of a catalyst comprising a tungstophosphoric acid of which 10–90% of the total amount of proton is replaced with a member selected from the group consisting of (a) cesium metal cation, (b) a combination of cesium metal cation and at least one cation selected from alkali metal cations other than cesium cation, and (c) a combination of cesium metal cation and at least one cation of iron group metal cations.

The catalyst used in the present invention may be a tungstophosphoric acid type heteropoly acid in the form such that 10–90% of hydrogen atoms (substantially in the form of hydrogen cation) of a tungstophosphoric acid of the general formula:

$$(M_1)_a(P)_b(W)_c(O)_d(H)_e$$

where
$M_1$ is vanadium atom or boron atom,
P is phosphorus atom, W is tungsten atom,
O is oxygen atom, and H is hydrogen atom;
a is an integer of 0, 1 and 2, b is an integer of 1 and 2,
c is a positive integer of 20 or less, d is a positive integer of 100 or less and e is a positive integer of 10 or less,
is replaced with
(a) cesium metal (substantially cesium metal cation),
(b) both cesium metal (substantially cesium metal cation other than cesium, or
(c) both cesium metal (substantially cesium metal cation) and at least one iron group metal (substantially iron group metal cation).

Particularly preferable catalysts include a tungstophosphoric acid where "a" is zero, and a vanadium-containing tungstophosphoric acid where $M_1$ is vanadium atom, proton of these acids being partly replaced with the above-mentioned metal cation or cations.

The process of the present invention is explained in the following in detail.

Ethylene used in the process of the present invention is not particularly necessary to be purified, and may be that having a purity of a general reagent grade, or that available as an ordinary industrial product. Further, it does not matter that an impurity such as ethane or the like is contained.

Acetic acid used in the process of the present invention is not particularly required to be purified.

Acetic acid having a purity of an ordinary reagent grade may be used as it is, and acetic acid available as an ordinary industrial chemical may be used.

The catalyst used in the process of the present invention may be: a tungstophosphoric acid type heteropoly acid in the form such that 10–90% of hydrogen atom (substantially hydrogen cation) or a tungstophosphoric acid is replaced with (a) cesium metal (substantially cesium cation) and represented by the general formula, $$(M_1)_a(P)_b(W)_c(O)_d(H)_{e-f}(Cs)_f$$

where
$M_1$, P, W, O, H, a, b, c, d and e are as defined above,
Cs is cesium atom,
f is a positive real number and
f=0.1e–0.9e;
a tungstophosphoric acid type heteropoly acid in the form such that 10–90% of hydrogen atom (substantially hydrogen cation) of a tungstophosphoric acid is replaced with (b) cesium metal (substantially cesium metal cation) and at least one alkali metal (substantially alkali metal cation) other than cesium and represented by the general formula, $$(M_1)_a(P)_b(W)_c(O)_d(H)_{e-f-g}(Cs)_f(M_2)_g$$

where
$M_1$, P, W, O, H, Cs, a, b, c, d, and e are as defined above, $M_2$ is one or two or more of alkali metal atoms selected from alkali metal atoms other than cesium, f' and g are positive real numbers, and f'+g=0.1e-0.9e;

or a tungstophosphoric acid type heteropoly acid in the form such that 10-90% of hydrogen atom (substantially hydrogen cation) of a tungstophosphoric acid is replaced with (c) cesium metal (substantially cesium metal cation) and at least one iron group metal (substantially iron group metal cation), and represented by the general formula, $$(M_1)_a(P)_b(W)_c(O)_d(H)_{e-f'-mg'}(Cs)_{f'}(M_3)_{g'}$$

where $M_1$, P, W, O, H, Cs, a, b, c, d, and e are as defined above, $M_3$ is one or two or more of iron group metal atoms, m is a valence of iron group metal, f' and g' are positive real numbers, and f'+mg'=0.1e-0.9e.

In particular, the following are the most easily available heteropoly acids:

a heteropoly acid in the form such that 10-90% of proton of dodecatungstophosphoric acid ($PW_{12}O_{40}H_3$) is replaced with (a) cesium cation and represented by the formula, $$PW_{12}O_{40}H_{3-f}Cs_f$$

(f=0.3-2.7);

a heteropoly acid in the form such that 10-90% of proton of dodecatungstophosphoric acid ($PW_{12}O_{40}H_3$) is replaced with (b) cesium cation and at least one alkali metal cation other than cesium cation and represented by the formula, $$PW_{12}O_{40}H_{3-f-g}Cs_f M_g$$

(f+g=0.3-2.7,

M is one or two or more of alkali metal atoms other than cesium);

a heteropoly acid in the form such that 10-90 % of proton of dodecatungstophosphoric acid ($PW_{12}O_{40}H_3$) is replaced with (c) cesium metal cation and at least one iron group metal cation and represented by the formula, $$PW_{12}O_{40}H_{3-f'-mg'}Cs_{f'}M'_{g'}$$

where f'+mg'=0.3-2.7,

M' is one or two or more of iron group metal atoms, m is a valence of iron group metal, when iron group metals are present in the two or more valence states, m is the average valence; and heteropoly acids having a structure such that one or more of tungsten atoms of the above-mentioned compounds are replaced with vanadium atoms.

In the following, there is explained the degree of replacement at which the proton of a tungstophosphoric acid is replaced with (a) cesium metal cation, (b) cesium metal cation and at least one alkali metal cation other than cesium cation, or (c) cesium metal cation and at least one iron group metal cation.

The degree of replacement at which the proton is replaced with cesium metal cation, cesium metal cation and alkali metal cation other than cesium cation, or cesium cation and iron group cation is such that 10-90% of proton of a heteropoly acid is replaced with the above-mentioned metal cation (cesium cation alone, or both cesium cation and other metal cation). The degree of replacement is preferably 30-90%, more preferably 50-85%.

When the degree of replacement is too low, the tungstophosphoric acid can not be substantially a solid catalyst, and the catalytic activity is low. On the contrary, when the degree of replacement is too high, the amount of proton of the heteropoly acid decreases and thereby the function as an acid catalyst decreases.

When two or more kinds of metal cations are used for replacement, the sum of the cations is required to be within the above-mentioned range. Though the composition of cations are not particularly limited, in any case preferably at least 10%, more preferably at least 30% of proton is replaced with cesium cation.

When the proton of a tungstophosphoric acid is replaced with a divalent or higher valent metal cations, in the present invention the degree of replacement is calculated assuming that the number of proton corresponding to the valence number of the metal is replaced with the metal.

According to the present invention, there may be used any process for effecting the method for replacing the proton of the heteropoly acid with (a) cesium metal cation, (b) cesium metal cation and at least one cation selected from alkali metal cations other than cesium cation, or (c) cesium metal cation and at least one cation selected from iron group metal cations, as far as the proton can be replaced with the above-mentioned metal cation.

As an easily practicable method, there may be mentioned a method of mixing, with stirring, a solution of a tungstophosphoric acid such as an aqueous solution thereof and the like with (a) a solution of a cesium compound, (b) respective solutions of a cesium compound and at least one alkali metal compound other than a cesium compound, or (c) respective solutions of a cesium compound and at least one iron group metal compound. Here it is recommended as a preferable replacing method that the proton of a tungstophosphoric acid is firstly replaced with cesium cation and then the remaining proton is replaced with each of other cations in case of replacing the proton with cesium cation and at least one alkali metal cation other than cesium cation, or replacing the proton with cesium cation and an iron group metal cation.

As cesium compounds, there may be used any cesium compound without particular limitation in the present invention, but examples of easily available compounds include cesium acetate, cesium carbonate, cesium phosphate, and cesium hydroxide.

By using these compounds, the proton of a tungstophosphoric acid can be easily replaced with cesium cation.

Alkali metals other than cesium as mentioned in the present invention are lithium, sodium, potassium, rubidium, and francium. Easily available alkali metal compounds are alkali metal carbonates, bicarbonates, hydroxides, acetates and the like though not limited thereto.

By using these compounds, proton of tungstophosphoric acid can be easily replaced with alkali metal cations.

What is meant by iron group metal in the process of the present invention is iron, cobalt and nickel. Though not limited, easily available compounds thereof are acetates, phophates and the like. By using such compounds, proton of a tungstophosphoric acid can be easily replaced with iron group metal cation.

According to the process of the present invention, the reaction of ethylene and acetic acid to produce ethyl acetate proceeds as an addition reaction. The reaction form may be a so-called liquid phase reaction where acetic acid is reacted in a liquid phase, or a gas phase reaction where ethylene and acetic acid are reacted in a gas phase.

In addition, with respect to the reaction pressure, the reaction may be carried out under any of reduced pressure, atmospheric pressure and high pressure, and in a gas phase, a pressure of 0–20 kg/cm$^2$G is preferable while in a liquid phase, a pressure of 30–300 kg/cm$^2$G is preferable.

With respect to the reaction system, it is not particularly limited, and a continuous flow, batch or semi-batch system may be used.

When the reaction is carried out in a gas phase, a more desirable result can be obtained by adding and introducing water into the reaction system as well as the starting materials, i.e. ethylene and acetic acid. In other words, water functions to increase the reaction activity.

When the method of the present invention is carried out by adding water to the reaction system, the amount to be added is not particularly limited, but the weight of water is preferably 20% or less, more preferably 0.01–10% based on the total weight acetic acid and water.

When the amount of water is too much, the reaction velocity is liable to be lowered due to the dilution of the reaction starting material.

In carrying out the process of the present invention, there may be added solvents, additives and diluents inert to the catalysts and the reaction reagents (starting materials and products).

For example, the following materials may be added to the reaction zone as solvents or diluents:
aliphatic saturated hydrocarbons such as
n-butane,
n-pentane,
n-hexane,
n-heptane,
n-octane,
n-nonane,
n-decane,
and the like;
aromatic hydrocarbons such as
benzene,
toluene,
ethylbenzene,
xylene,
anisole,
cumene,
nitrobenzene,
and the like;
alicyclic saturated hydrocarbons such as
cyclopentane,
alkyl-substituted cyclopentanes,
alkoxy-substituted cyclopentanes,
nitro-substituted cyclopentanes,
cyclohexane,
alkyl-substituted cyclohexanes,
alkoxy-substituted cyclohexanes,
nitro-substituted cyclohexanes,
cycloheptane,
alkyl-substituted cycloheptanes,
alkoxy-substituted cycloheptanes,
nitro-substituted cycloheptanes,
cyclooctane,
alkyl-substituted cyclooctanes,
alkoxy-substituted cyclooctanes,
nitro-substituted cyclooctanes,
and the like;
nitrogen,
argon,
air,
helium,
and the like.

According to the process of the present invention, the amount relation between acetic acid and ethylene is not particularly limited, but from the standpoint of industrial production efficiency, the amount ratio of acetic acid/ethylene of 0.1–100 (molar ratio) is recomendable.

For example, in order to attain a high conversion of acetic acid, it is preferable to carry out the reaction at a molar ratio of ethylene to acetic acid of 1 or more.

On the contrary, in order to attain a high conversion of ethylene, it is preferable to effect the reaction at a molar ratio of acetic acid to ethylene of 1 or more.

In the process of the present invention, it is not always necessary to conduct the reaction within the above-mentioned amount ratio of the starting materials, but the reaction may be effected outside the above-mentioned range.

When the process of the present invention is carried out, the amount of the catalyst is not particularly limited. For example, in the case where the liquid phase reaction is carried out batchwise, it is recommendable to practice the process in the presence of the catalyst in an amount of 0.1–100% by weight, preferably 1–50% by weight based on acetic acid fed since this procedure is easy to carry out.

In the case that the amount of the catalyst is 0.1% by weight or less, the reaction proceeds slowly while in the case of using the catalyst in an amount of 100% by weight or more, the reaction proceeds sufficiently, but it is not preferable from an economical point of view.

However, it is sure that the present invention can be effected outside the above-mentioned amount range of the catalyst.

Further, when the process is carried out in a gas phase continuous flow reaction, it is natural that the contact time between the catalyst and the reaction reagents is more important than the amount of the catalyst.

According to the present invention, the reaction temperature is not particularly critical and the process can be carried out in a wide range of temperature, preferably 50° C.–500° C., more preferably 100° C.–300° C. At a too low temperature, the reaction speed is lowered. On the contrary, at a too high temperature, many side reactions occur and further, the product is decomposed (a reverse reaction proceeding to form ethylene and acetic acid) and therefore, the reaction can not effectively proceeds.

According to the process of the present invention, the reaction time (the contact time with the catalyst in a gas phase continuous flow reaction) is not particularly limited, but, for example, in a liquid phase batch reaction, the reaction time depends on the amount of catalyst and reaction temperature. When the amount of catalyst is large and the temperature is high, the reaction time is very short (about several seconds or less). On the contrary, when the amount of catalyst is small and the temperature is low, the reaction time is long (about 24 hours).

The contact time in a gas phase continuous flow reaction is not also particularly limited. However, when the contact time is too short, the reaction proceeds slowly. On the contrary, when the contact time is unnecessarily long, side reactions proceed and unnecessarily large amount of the catalyst is used. Therefore, neither too short nor too long contact time is preferable.

The contact time is preferably 0.02 sec.-10 min., more preferably 0.5 sec.-1 min. in a gas phase continuous flow reaction.

After completion of the reaction, the end product may be separated from the starting materials and others by a separating operation such as ordinary distillation operation.

According to the present invention, ethyl acetate can be efficiently produced by carrying out the reaction of ethylene with acetic acid in a liquid or gas phase in the presence of a catalyst composed of a tungstophosphoric acid of which 10-90% of the total amount of proton is replaced with (a) cesium cation, (b) a combination of cesium cation and alkali metal cation other than cesium, or (c) a combination of cesium cation and iron group metal cation.

The efficiency of producing ethyl acetate can be further improved by the coexistence of water in the reaction system, for example, by introducing water into the reaction system in the gas phase reaction. In this case, the catalyst exhibits a higher catalytic activity when about 80% of the proton is replaced with cesium cation, about 2% of the proton is replaced with an alkali metal cation other than cesium or an iron group metal cation and the weight of water is 3% based on the total weight of acetic acid fed and water.

According to the process of the present invention, the catalyst can retain the catalytic activity substantially free from deterioration even when the reaction is carried out for a long period of time. The catalyst can be used as a durable catalyst in the industrial production.

As a result, the present invention provides an effective process for producing ethyl acetate capable of overcoming disadvantages of conventional catalysts such as low catalytic activity and lack of durability of catalyst and the like.

According to the present invention, ethyl acetate can be produced from ethylene and acetic acid in good conversion and good selectivity in a liquid phase or gas phase reaction. The catalyst may be used as a liquid phase heterogeneous catalyst or a gas phase solid catalyst. The catalyst can be easily recovered.

Further, according to the process of the present invention, materials of the machine and apparatus used for the production such as a reactor and other installation are not adversely affected, e.g. the corrosion is inhabited or suppressed.

In the following, the process of the present invention is explained further in detail referring to the examples, but it is to be understand that they are given for the purpose of illustration and not limitation.

(1) Quantitative Analysis of the Reaction Product

1—1. Liquid Phase Reaction

After carrying out the reaction for a prescribed time at a prescribed temperature, the reaction product was cooled to room temperature and the reaction fluid was quantitatively analyzed by chromatography.

1-2. Gas Phase Continuous Flow Reaction

After carrying out the reaction for a prescribed time at a prescribed temperature, the reaction product was cellected in a reaction gas liquefying vessel in a liquid state. This liquid was quantitatively analyzed by chromatography.

(2) Partly Replacing Proton of Dodecatungstophosphoric Acid ($PW_{12}O_{40}H_3$) with Cesium Cation While a prescribed amount of an aqueous solution of dodecatungstophosphoric acid is stirred, to the aqueous solution was added gradually a prescribed amount of an aqueous solution of carbonate or cesium acetate. As the addition started, a white precipitate started to form in the stirred solution. After finishing the addition of the cesium compound, the stirring was continued for further two hours. The resulting product was dehydrated and dried at 80° C. under reduced pressure to obtain a white solid matter. The product was used as a catalyst. Further, the solid matter which was dried at 350° C. in an electric furnace was also used as a catalyst. The catalysts used in the following examples are those dried at 350° C. unless otherwise specified.

(3) Calculation of the Amount of Proton of Dodecatungstophosphoric Acid Replaced with Cesium Cation This amount is a ratio of the total number of cesium atoms of a cesium compound used for exchange (B mg atom) to the total number of hydrogen atom of a dodecatungstophosphoric acid used for exchange (A mg atom), and is calculated by the following formula.

Calculation formula(%) = 100 × (B/A)

Therefore, the replaced amount is an average value.

(4) Partly Replacing Proton of Dodecatungstophosphoric Acid with Cesium Cation and Alkali Metal Cation other than Cesium Cation While a prescribed amount of an aqueous solution of dodecatungstophosphoric acid is stirred, to the aqueous solution was added gradually a prescribed amount of an aqueous solution of cesium carbonate or cesium acetate. As the addition started, a white precipitate started to form in the stirred solution. After finishing the addition of the cesium compound, the stirring was continued for further two hours.

Then, a prescribed amount of an aqueous solution of a carbonate of an alkali metal other than cesium was added to the white suspension liquid and stirring was continued for further two hours followed by removing water from the separated precipitate by evaporation.

The resulting product was dehydrated and dried at 80° C. under reduced pressure to obtain a white solid matter. Then, the solid matter which was dried further at 350° C. in an electric furnace was used as a catalyst.

(5) Calculation of the Amount of Proton of Dodecatungstophosphoric Acid Replaced with Cesium Cation and Alkali Metal Cation other than Cesium This amount is a ratio of the sum of the total number of cesium atom of a cesium compound used for exchange (B mg atom) and the total number of alkali metal atom of a carbonate of an alkali metal other than cesium used for exchange (C mg atom) to the total number of hydrogen atom of dodecatungstophosphoric acid used for exchange (A mg atom), and is calculated by the following formula.

Calculation formula(%) = 100 × ((B+C)/A)

Therefore, the replaced amount is an average value.

(6) Partly Replacing Proton of Dodecatungstophosphoric Acid with Cesium Cation and Iron Group Metal Cation While a prescribed amount of an aqueous solution of dodecatungstophosphoric acid is stirred, to the aqueous solution was added gradually a prescribed amount of an aqueous solution of cesium carbonate or cesium acetate. As the addition started, a white precipitate started to form in the stirred solution. After finishing the addition of the cesium compound, the stirring was continued for further two hours.

Then, a prescribed amount of an aqueous solution of an acetate of an iron group metal (acetate of the divalent metal) was added to the resulting white liquid suspension, and stirring was continued for further two hours, and then the separated precipitate was subjected to evaporation to remove water. The product was dehydrated and dried at 80° C. under reduced pressure to give a white solid matter.

This solid matter was dried at 350° C. in an electric furnace and the product thus dried was used as a catalyst.

(7) Calculation of the Amount of Proton of Dodecatungstophosphoric Acid Replaced with Cesium Cation and an Iron Group Metal Cation (Divalent)

This amount is a ratio of the sum of the total number of cesium atom of a cesium compound used for exchange (B mg atom) and the total number of iron group metal atom of an iron group metal compound used for exchange (C mg atom) to the total number of hydrogen atoms of dodecatungstophosphoric acid used for exchange (A mg atom), and is calculated by the following formula.

Calculation formula(%) = 100 × ((B+2C)/A)

In the following examples, the yield of ethyl acetate was calculated based on the acetic acid fed.

EXAMPLE 1

In a 200 ml autoclave equipped with a magnetic stirrer were placed 3.0 g of 83.3% Cs cation exchanged dodecatungstophosph acid (containing average 4.2 molecules of water in one molecule of the heteropoly acid) not dried at 350° C. and 60.5 g of commercially available 99.5% acetic acid (manufactured by Kokusan Kagaku), and 0.69 mol of a commercially available 99.5% ethylene was pressurized into the reaction mixture to be slowly absorbed in the acetic acid.

The autoclave was heated with stirring at 500 r.p.m. to carry out the reaction at 180° C. for 5 hours. The results were: acetic acid conversion, 35.7% and yield of ethyl acetate, 35.5%.

COMPARATIVE EXAMPLES 1-4

The procedure of Example 1 was repeated to effect the reaction of acetic acid with ethylene except that 3.0 g of the catalyst in Table 1 was used in place of that in Example 1. The results are shown in Table 1. The yield of ethyl acetate was lower than that when the catalyst of the present invention was used.

TABLE 1

| Comparative Example | Catalyst | Acetic acid conversion (%) | Ethyl acetate yield (%) |
|---|---|---|---|
| 1 | Dodecatungstophosphoric acid | 2.4 | 2.1 |
| 2 | Dodecatungstosilicic acid | 4.9 | 4.6 |
| 3 | H-ZSM 5 | 3.7 | 3.1 |
| 4 | Al bentonites (Al = 19.4%) | 2.2 | 1.3 |

EXAMPLES 2-3

A Pyrex reaction pipe of 1 cm in inner diameter was packed with 5 ml of a catalyst composed of dodecatungstophosphoric acid of which 83.3% of proton was replaced with cesium ion derived from cesium carbonate. The reactor was heated to 180° C. and kept at this temperature while acetic acid and ethylene were fed at 42 mmol/hr and 130 mmol/hr, respectively, and these reactants were thoroughly mixed through an evaporation heater and were brought into contact with the catalyst. The reaction gas after contacted with the catalyst was cooled and collected.

After passing the reactants for 3 hours and 6 hours, the respective collected reaction fluids were analyzed. The results in Table 2 show that ethyl acetate is obtained in good yield.

COMPARATIVE EXAMPLES 5-9

The procedure of Example 2 was repeated to carry out the reaction of acetic acid with ethylene except that a catalyst shown in Table 2 was used in place of the catalyst in Example 2. As is clear from the results shown in Table 2, each catalyst exhibited lower activity than the catalysts of the present invention.

In addition, the catalysts used in Comparative Examples 5-8 exhibited remarkable lowering of the catalytic activity even after 6 hours of the reaction.

TABLE 2

| | Catalyst | Passing time (hr.) | Yield of ethyl acetate (%) |
|---|---|---|---|
| Example 2 | PW-Cs (83.3) | 3.0 | 19.1 |
| Example 3 | PW-Cs (83.3) | 6.0 | 19.7 |
| Comparative Example 5 | Amberlyst 15 | 3.0 | 10.1 |
| Comparative Example 6 | Amberlyst 15 | 6.0 | 5.2 |
| Comparative Example 7 | Dodecatungstosilicic acid | 3.0 | 9.4 |
| Comparative Example 8 | Dodecatungstosilicic acid | 6.0 | 7.6 |
| Comparative Example 9 | H-ZSM-5 | 6.0 | 4.0 |

PW-Cs (83.3) is a catalyst composed of dodecatungstophosphoric acid of which 83.3% of proton is replaced with cesium cation.
H-ZSM-5 is a zeolite of a high silica proton type.

EXAMPLE 4

The procedure of Example 2 was repeated except that 5 ml of a catalyst composed of tungstophosphoric acid of which 83.3% of proton was replaced with cesium ion by using cesium acetate (PW-Cs-(83.3%)) was used. Ethyl acetate was produced in an 18.9% yield.

EXAMPLE 5

The procedure of Example 2 was repeated except that the reaction temperature was 200° C., and ethyl acetate was produced in a 24.5%.

EXAMPLE 6

The procedure of Example 2 was repeated to effect a reactants-passing reaction except that the reaction temperature was 150° C. Ethyl acetate was produced in a 11.4% yield.

EXAMPLES 7-8

The procedure of Example 2 was repeated except that the respective ethylene introducing rates were 65 mmol/hr and 260 mmol/hr. As shown in Table 3, ethyl acetate was produced in good yields in respective cases.

TABLE 3

|  | Ethylene introducing speed (mmol/hr.) | Yield of ethyl acetate (%) |
| --- | --- | --- |
| Example 7 | 65.0 | 15.3 |
| Example 8 | 260.0 | 16.2 |

EXAMPLE 9

The procedure of Example 2 was repeated except that the respective introducing rates of acetic acid and ethylene were twice those in Example 2. Ethyl acetate was produced in a 14.3% yield.

EXAMPLES 10-15

The procedure of Example 2 was repeated except that a catalyst composed of dodecatungstophosphoric acid (PW) of which 10, 30, 50, 70, 80 or 90% of proton was replaced with cesium cation was used. The results are shown in Table 4.

TABLE 4

|  | Proton exchange rate (x%) PW-Cs (x) | Yield of ethyl acetate (%) |
| --- | --- | --- |
| Example 10 | 10 | 7.5 |
| Example 11 | 30 | 8.9 |
| Example 12 | 50 | 10.7 |
| Example 13 | 70 | 14.8 |
| Example 14 | 80 | 20.1 |
| Example 15 | 90 | 8.4 |

PW-Cs (x) is a catalyst composed of a dodecatungstophosphoric acid of which x% of proton is replaced with cesium cation.

EXAMPLES 16-18

A SUS-316 reaction tube of 10 mm in inner diameter and 300 mm in length was packed with 20 ml of a catalyst composed of a dodecatungstophosphoric acid of which 83.3% of proton was replaced with cesium cation (PW-Cs (83.3)), heated to 180° C., and kept at this temperature while acetic acid and ethylene were introduced into an evaporator at feeding rates of 150 mmol/hr. and 450 mmol/hr., respectively, evaporated, mixed therein and introduced into the reaction tube to carry out the reaction.

The exhaust gas from the reaction tube was cooled and the cooled liquid was collected in a vessel, and after completion of the reaction, the reaction fluid was analyzed.

The reaction pressure was kept in the reaction tube at 2 kg/cm$^2$G, 5 kg/cm$^2$G and 10 kg/cm$^2$G, respectively, and the reaction was carried out for 6 hours.

The reaction results are shown in Table 5. The yield of ethyl acetate increased by increasing the reaction pressure.

TABLE 5

|  | Reaction pressure (kg/cm$^2$G) | Yield of ethyl acetate (%) |
| --- | --- | --- |
| Example 16 | 2 | 26.3 |
| Example 17 | 5 | 30.9 |
| Example 18 | 10 | 43.6 |

EXAMPLES 19-20

The procedures of Example 2 and Example 3 were repeated to effect the reactions for 3 hours and 6 hours, respectively except that water was added to the reaction tube at a flow rate of 0.08 g/hr. (the weight of water becoming 3% based on the total amount of acetic acid and water).

The results are shown in Table 6. Ethyl acetate was obtained in good yields. COMPARATIVE EXAMPLES 10-14

The procedures of Examples 19 and 20 were repeated to effect the reaction of acetic acid with ethylene for 3 hours or 6 hours except that the respective catalysts listed in Table 6 were used.

The results are shown in Table 6. The respective catalysts exhibited low activity as compared with the catalyst of the present invention. In addition, the catalysts used in Comparative Examples 10-13 showed a remarkable lowering of catalytic activity even during a short reaction time such as 6 hours.

TABLE 6

|  | Catalyst | Passing time (hr.) | Yield of ethyl acetate (%) |
| --- | --- | --- | --- |
| Example 19 | PW-Cs(83.3) | 3.0 | 24.9 |
| Example 20 | PW-Cs(83.3) | 6.0 | 25.2 |
| Comparative Example 10 | Amberlyst 15 | 3.0 | 8.4 |
| Comparative Example 11 | Amberlyst 15 | 6.0 | 3.7 |
| Comparative Example 12 | Dodecatungsto-silicic acid | 3.0 | 11.7 |
| Comparative Example 13 | Dodecatungsto-silicic acid | 6.0 | 6.8 |
| Comparative Example 14 | H-ZSM-5 | 6.0 | 5.2 |

PW-Cs(83.3) is a catalyst composed of a dodecatungstophosphoric acid of which 83.3% of proton was replaced with cesium cation. H-ZSM-5 is a zeolite of a high silica proton type.

EXAMPLES 21-24

The procedure of Example 20 was repeated to effect the reaction for 6 hours except that the respective feed rates of water were 0.01, 0.03, 0.13 and 0.25 g/hr.

As is clear from the results shown in Table 7, the respective additions of water resulted in increase of production of ethyl acetate.

TABLE 7

|  | Speed of introducing water (g/hr.) | Yield of ethyl acetate (%) |
| --- | --- | --- |
| Example 21 | 0.01 | 21.4 |
| Example 22 | 0.03 | 23.7 |
| Example 23 | 0.13 | 23.9 |
| Example 24 | 0.25 | 21.6 |

EXAMPLE 25

The procedure of Example 19 was repeated except that 5 ml of a catalyst composed of dodecatungstophosphoric acid of which 83.3% of proton was replaced with cesium ion derived from cesium acetate (PW-Cs (83.3)) was used.

Ethyl acetate was obtained in a 24.4% yield.

EXAMPLE 26

The procedure of Example 19 was repeated to effect a reactants-passing reaction except that the reaction temperature was 200° C. As a result, ethyl acetate was obtained in a 28.8% yield.

EXAMPLE 27

The procedure of Example 19 was repeated to effect a reactants-passing reaction except that the reaction temperature was 150° C. As a result, ethyl acetate was obtained in a 16.1%.

EXAMPLE 28

The procedure of Example 19 was repeated to effect that the reaction time (time during introducing starting materials) was 30 hours. Reaction fluid samples collected at every 6 hours were analyzed to determine the yield of ethyl acetate.

The results in Table 8 show that the catalyst still retained a sufficient activity even after 30 hours of reaction.

TABLE 8

| No. | Lap sample (hr.-hr.) | Yield of ethyl acetate (%) |
| --- | --- | --- |
| 1 | 0–6 | 24.8 |
| 2 | 6–12 | 25.5 |
| 3 | 12–18 | 24.9 |
| 4 | 18–24 | 25.1 |
| 5 | 24–30 | 25.3 |

COMPARATIVE EXAMPLE 15

The procedure of Example 28 was repeated except that Amberlyst 15 was used, the reaction time (time during introducing the starting materials) was 12 hours and the reaction fluid was sampled at every 3 hours to analyze and determine the yield of ethyl acetate. The result in Table 9 shows activity of this catalyst was remarkably lowered after 6 hours of reaction.

TABLE 9

| No. | Lap sample (hr.-hr.) | Yield of ethyl acetate (%) |
| --- | --- | --- |
| 1 | 0–3 | 9.4 |
| 2 | 3–6 | 1.7 |
| 3 | 6–9 | 1.1 |
| 4 | 9–12 | 0.7 |

EXAMPLES 29-30

The procedure of Example 19 was repeated except that the respective ethylene introducing speeds were 65 mmol/hr. and 260 mmol/hr. The results in Table 10 shows that ethyl acetate was produced in good yield in each case.

TABLE 10

| | Speed of introducing ethylene (mmol/hr) | Yield of ethyl acetate (%) |
| --- | --- | --- |
| Example 29 | 65.0 | 21.4 |
| Example 30 | 260.0 | 23.8 |

EXAMPLE 31

The procedure of Example 19 was repeated except that the introducing speed of each of acetic acid, water and ethylene was twice that in Example 19. As a result, ethyl acetate was produced in a 19.7% yield.

EXAMPLES 32-37

The procedure of Example 19 was repeated except that there was used a catalyst composed of a tungstophosphoric acid (PW) in which 10, 30, 50, 70, 80 or 90% of the proton was replaced with cesium cation. The results are shown in Table 11.

TABLE 11

| | Proton exchanging rate (x%) PW-Cs (x) | Yield of ethyl acetate (%) |
| --- | --- | --- |
| Example 32 | 10 | 11.2 |
| Example 33 | 30 | 13.7 |
| Example 34 | 50 | 16.4 |
| Example 35 | 70 | 20.9 |
| Example 36 | 80 | 26.3 |
| Example 37 | 90 | 13.2 |

PW-Cs (x) is a catalyst composed of a dodecatungstophosphoric acid of which x% of proton is replaced with cesium cation.

EXAMPLES 38-40

The procedure of each of Examples 16-18 was repeated to effect the continuous flow reaction under pressurized condition except that water was added at a flow rate of 0.28 g/hr.

The results in Table 12 show that the yield of ethyl acetate increased as the reaction pressure increased.

TABLE 12

| | Reaction pressure (kg/cm$^2$G) | Yield of ethyl acetate (%) |
| --- | --- | --- |
| Example 38 | 2 | 30.7 |
| Example 39 | 5 | 34.2 |
| Example 40 | 10 | 47.4 |

EXAMPLES 41-42

The procedure of Example 19 or 20 was repeated except that there was used 5 ml of a catalyst composed of dodecatungstophosphoric acid, 80.0% of proton of said acid being replaced with cesium ion by using cesium carbonate and then 2.0% of proton thereof being replaced with potassium cation by using potassium carbonate.

The results are shown in Table 13. Ethyl acetate was formed in good yields.

TABLE 13

| | Catalyst | Passing time (hr.) | Yield of ethyl acetate (%) |
| --- | --- | --- | --- |
| Example 41 | PW-Cs(80.0)-K(2.0) | 3.0 | 28.7 |
| Example 42 | PW-Cs(80.0)-K(2.0) | 6.0 | 29.1 |

PW-Cs(80.0)-K(2.0) is a catalyst composed of a dodecatungstophosphoric acid in which 80.0% of proton is replaced with cesium cation and then 2% of proton is replaced with potassium ion.

EXAMPLES 43-46

The procedure of Example 42 was repeated to effect the reaction for 6 hours except that feed rates of water were changed to 0.01, 0.30, 0.13 and 0.25 g/hr, respectively. Table 14 shows the results. Ethyl acetate was formed in good yields.

TABLE 14

|  | Water introducing speed (g/hr.) | Yield of ethyl acetate (%) |
|---|---|---|
| Example 43 | 0.01 | 22.8 |
| Example 44 | 0.03 | 26.9 |
| Example 45 | 0.13 | 27.7 |
| Example 46 | 0.25 | 23.0 |

EXAMPLE 47

The procedure of Example 41 was repeated except that there was used 5 ml of a catalyst prepared by replacing 80.0% of proton of dodecatungstophosphoric acid with cesium ion by using cesium acetate and then replacing 2% of proton with potassium ion by using potassium carbonate (PW-Cs (80)-K(2)). Ethyl acetate was formed in a 28.3% yield.

EXAMPLE 48

The procedure of Example 41 was repeated except that the reaction temperature was 200° C. Ethyl acetate was produced in a 31.2% yield.

EXAMPLE 49

The procedure of Example 41 was repeated to effect a reactants-passing reaction except that the reaction temperature was 150° C. Ethyl acetate was formed in a 17.4% yield.

EXAMPLE 50

The procedure of Example 41 was repeated except that the reaction time (starting materials-introducing time) was 30 hours and the reaction fluid was sampled every 6 hours for analyzing and determining the yield of ethyl acetate. The result is shown in Table 15. The catalyst still retained a sufficient activity even after 30 hours of the reaction.

TABLE 15

| No. | Lap sample (hr.-hr.) | Yield of ethyl acetate (%) |
|---|---|---|
| 1 | 0-6 | 28.8 |
| 2 | 6-12 | 29.2 |
| 3 | 12-18 | 29.0 |
| 4 | 18-24 | 28.6 |
| 5 | 24-30 | 29.3 |

EXAMPLES 51-52

The procedure of Example 41 was repeated except that the ethylene introducing speed was 65 mmol/hr. or 260 mmol/hr. Table 16 shows the results.

TABLE 16

|  | Ethylene introducing speed (mmol/hr.) | Yield of ethyl acetate (%) |
|---|---|---|
| Example 51 | 65.0 | 23.7 |
| Example 52 | 260.0 | 25.6 |

EXAMPLE 53

The procedure of Example 41 was repeated except that the introducing speed of acetic acid, water or ethylene was twice that in Example 41. As a result, ethyl acetate was formed in a 22.9% yield.

EXAMPLES 54-56

The procedure of Example 41 was repeated to effect the reaction for 3 hours except that there was used a catalyst prepared by replacing 80% of proton of dedecatungstophosphoric acid with cesium cation and then replacing 2% of proton with lithium cation by using lithium carbonate, sodium cation by using sodium carbonate, and rubidium cation by using rubidium carbonate, respectively in place of potassium cation.

As shown in Table 17, ethyl acetate was formed in good yield in each case.

TABLE 17

|  | M(alkali cation) PW-Cs(80.0)-M(2.0) | Yield of ethyl acetate (%) |
|---|---|---|
| Example 54 | Li+ | 28.4 |
| Example 55 | Na+ | 27.9 |
| Example 56 | Rb+ | 28.7 |

EXAMPLES 57-62

The procedure of Example 41 was repeated except that there was used a catalyst prepared by replacing proton of dodecatungstophosphoric acid with cesium cation and potassium cation.

As shown in Table 18, ethyl acetate was formed in a yield varying depending on the rate of exchanging proton with cesium cation and potassium cation.

TABLE 18

|  | Proton exchange rate (%) | | Yield of ethyl acetate (%) |
|---|---|---|---|
|  | Cs | K |  |
| Example 57 | 80 | 0.5 | 29.8 |
| Example 58 | 80 | 5.0 | 28.2 |
| Example 59 | 50 | 2.0 | 22.7 |
| Example 60 | 70 | 2.0 | 25.9 |
| Example 61 | 30 | 15.0 | 18.6 |
| Example 62 | 90 | 0.5 | 15.4 |

EXAMPLES 63-65

The procedure of each of Examples 38-40 was repeated to effect a pressurized flow reaction under the pressure shown in Table 19 except that the catalyst used in Example 41 was used. As is clear from the results in Table 19, the yield of ethyl acetate increased as the reaction pressure increased.

TABLE 19

|  | Reaction pressure (kg/cm$^2$G) | Yield of ethyl acetate (%) |
|---|---|---|
| Example 63 | 2 | 33.5 |
| Example 64 | 5 | 37.9 |
| Example 65 | 10 | 49.8 |

EXAMPLES 66-67

The procedure of Example 19 or 20 was repeated except that there was used 5 ml of a catalyst prepared by replacing 80% of proton of dodecatungstophosphoric acid with cesium ion by using cesium carbonate and then replacing 2% of proton with iron cation by using iron (II) acetate.

As shown in Table 20, ethyl acetate was obtained in good yields.

TABLE 20

| | Catalyst | Passing time (hr.) | Yield of ethyl acetate (%) |
|---|---|---|---|
| Example 66 | PW-Cs(80.0)-Fe(2) | 3.0 | 29.2 |
| Example 67 | PW-Cs(80.0)-Fe(2) | 6.0 | 29.4 |

PW-Cs(80.0)-Fe(2) is a catalyst prepared by replacing 80% of proton of docecatungstophosphoric acid with cesium ion and then replacing 2% of proton thereof with divalent iron cation.

EXAMPLES 68-71

The procedure of Example 67 was repeated to effect the reaction for 6 hours except that the water introducing rate was changed to 0.01, 0.03, 0.13 and 0.25 g/hr respectively.

As shown in Table 21, ethyl acetate was obtained in good yield in each case.

TABLE 21

| | Water introducing speed (g/hr.) | Yield of ethyl acetate (%) |
|---|---|---|
| Example 68 | 0.01 | 23.1 |
| Example 69 | 0.03 | 28.3 |
| Example 70 | 0.13 | 29.0 |
| Example 71 | 0.25 | 24.1 |

EXAMPLE 72

The procedure of Example 66 was repeated except that there was used 5 ml of a catalyst prepared by replacing 80% of proton with cesium ion by using cesium acetate and then replacing 2% of proton of dodecatungstophosphoric acid with divalent iron cation by using iron (II) acetate (PW-Cs(80.0)-Fe(2)). Ethyl acetate was produced in a 28.8% yield.

EXAMPLE 73

The procedure of Example 66 was repeated to effect the reactants-passing reaction except that the reaction temperature was 200° C. Ethyl acetate was obtained in a 31.9% yield.

EXAMPLE 74

The procedure of Example 66 was repeated to effect the reactants-passing reaction except that the reaction temperature was 150° C. Ethyl acetate was obtained in a 17.7% yield.

EXAMPLE 75

The procedure of Example 66 was repeated except that the reaction time (starting materials-introducing time) was 30 hours and the reaction fluid was sampled every 6 hours for analyzing and determining the yield of ethyl acetate. The result is shown in Table 22. The catalyst still retained a sufficient activity even after 30 hours of the reaction.

TABLE 22

| No. | Lap sample (hr.-hr.) | Yield of ethyl acetate (%) |
|---|---|---|
| 1 | 0-6 | 29.5 |
| 2 | 6-12 | 29.3 |
| 3 | 12-18 | 29.7 |
| 4 | 18-24 | 28.9 |

TABLE 22-continued

| No. | Lap sample (hr.-hr.) | Yield of ethyl acetate (%) |
|---|---|---|
| 5 | 24-30 | 29.4 |

EXAMPLES 76-77

The procedure of Example 66 was repeated except that the ethylene introducing rate was 65 mmol/hr. and 260 mmol/hr, respectively. As shown in Table 23. Each good yield of ethyl acetate was confirmed.

TABLE 23

| | Ethylene introducing speed (mmol/hr.) | Yield of ethyl acetate (%) |
|---|---|---|
| Example 76 | 65.0 | 25.1 |
| Example 77 | 260.0 | 26.9 |

EXAMPLE 78

The procedure of Example 66 was repeated except that the introducing rate of each of acetic acid, water and ethylene was twice that in Example 66. Ethyl acetate was obtained in a 23.3% yield.

EXAMPLES 79-80

The procedure of Example 66 was repeated to effect the reaction for 3 hours except that there was used a catalyst prepared by replacing 80 % of proton of dodecatungstophosphoric acid with cesium cation and then replacing 2% of proton with nickel cation by using nickel acetate or cobalt cation by using cobalt acetate (each divalent compound) in place of iron cation used for replacing in Example 66.

As shown in Table 24, ethyl acetate was obtained in good yield each.

TABLE 24

| | PW-Cs(80.0)-M(2) (M = iron group metal) | Yield of ethyl acetate (%) |
|---|---|---|
| Example 79 | $Ni^{2+}$ | 28.8 |
| Example 80 | $Co^{2+}$ | 28.4 |

EXAMPLES 81-86

The procedure of Example 66 was repeated except that there was used a catalyst prepared by replacing proton of dodecatungstophosphoric acid with cesium ion and iron divalent cation (using cesium carbonate and iron acetate).

As shown in Table 25, ethyl acetate was produced in good yield in each case though varying depending on the amount of replaced proton.

TABLE 26

| | Proton exchange rate (%) | | Yield of ethyl acetate (%) |
|---|---|---|---|
| | Cs | Fe(II) | |
| Example 81 | 80 | 0.5 | 29.9 |
| Example 82 | 80 | 5.0 | 28.5 |
| Example 83 | 50 | 2.0 | 23.2 |
| Example 84 | 70 | 2.0 | 26.6 |
| Example 85 | 30 | 15.0 | 19.1 |
| Example 86 | 90 | 0.5 | 15.7 |

EXAMPLES 87-89

The procedure of each of Examples 38-40 was repeated to effect a pressurized flow reaction under each pressure except that 20 ml of the catalyst used in Example 66 was employed.

As shown in Table 26, it was confirmed that the yield of ethyl acetate increased by increasing the reaction pressure.

TABLE 26

| | Reaction pressure ($kg/cm^2G$) | Yield of ethyl acetate (%) |
|---|---|---|
| Example 87 | 2 | 34.2 |
| Example 88 | 5 | 39.0 |
| Example 89 | 10 | 51.3 |

What is claimed is:

1. A process for producing ethyl acetate which comprises reacting ethylene with acetic acid in the presence of a catalyst comprising a tungstophosphoric acid of which 10-90% of the total amount of proton is replaced with a member selected from the group consisting of (a) cesium metal cation, (b) a combination of cesium metal cation and at least one cation selected from alkali metal cations other than cesium cation, and (c) a combination of cesium metal cation and at least one cation of iron group metal cations.

2. The process according to claim 1 in which ethylene is reacted with acetic acid in a liquid phase where acetic acid is present in the presence of the catalyst comprising a tungstophosphoric acid of which 10-90% of the total amount of proton is replaced with cesium metal cation.

3. The process according to claim 1 in which ethylene is reacted with acetic acid in a gas phase in the presence of the catalyst comprising a tungstophosphoric acid of which 10-90% of the total amount of proton is replaced with cesium metal cation.

4. The process according to claim 3 in which ethylene is reacted with acetic acid in a gas phase in the presence of water.

5. The process according to claim 1 in which ethylene is reacted with acetic acid in a gas phase in the presence of water and the catalyst comprising a tungstophosphoric acid of which 10-90% of the total amount of proton is replaced with a combination of cesium metal cation and at least one cation selected from alkali metal cations other than cesium cation.

6. The process according to claim 1 in which ethylene is reacted with acetic acid in a gas phase in the presence of water and the catalyst comprising a tungstophosphoric acid of which 10-90% of the total amount of proton is replaced with a combination of cesium metal cation and at least one cation selected from iron group metal cations.

7. The process according to claim 5 in which the alkali metal cations other than cesium cation are lithium, sodium, potassium and rubidium metal cations.

8. The process according to claim 6 in which the tungstophosphoric acid is dodecatungstophosphoric acid 9. The process according to claim 1 in which the alkali metal cations other than cesium cation are lithium, sodium, potassium and rubidium metal cations.

10. The process according to claim 1 in which the tungstophosphoric acid is dodecatungstophosphoric acid.

11. The process according to claim 2 in which the tungstophosphoric acid is dodecatungstophosphoric acid.

12. The process according to claim 3 in which the tungstophosphoric acid is dodecatungstophosphoric acid.

13. The process according to claim 4 in which the tungstophosphoric acid is dodecatungstophosphoric acid.

14. The process according to claim 5 in which the tungstophosphoric acid is dodecatungstophosphoric acid.

15. A catalyst for producing ethyl acetate by reacting ethylene with acetic acid which comprises a tungstophosphoric acid of which 10-90 % of the total amount of proton is replaced with a member selected from the group consisting of (a) cesium metal cation, (b) a combination of cesium metal cation and at least one cation selected from alkali metal cations other than cesium cation, and (c) a combination of cesium metal cation and at least one cation of iron group metal cations.

* * * * *